US011273074B1

(12) United States Patent
Homer

(10) Patent No.: US 11,273,074 B1
(45) Date of Patent: Mar. 15, 2022

(54) SYSTEMS AND METHODS FOR FOR PHYSICAL AND ELECTRONIC SECURITY OF MEDICAL DEVICES

(71) Applicant: STROMA MEDICAL CORPORATION, Irvine, CA (US)

(72) Inventor: Gregg Homer, Irvine, CA (US)

(73) Assignee: Stroma Medical Corporation, Irvine, CA (US)

( * ) Notice: Subject to any disclaimer, the term of this patent is extended or adjusted under 35 U.S.C. 154(b) by 0 days.

(21) Appl. No.: 17/238,084

(22) Filed: Apr. 22, 2021

Related U.S. Application Data

(60) Provisional application No. 63/165,687, filed on Mar. 24, 2021.

(51) Int. Cl.
*A61F 9/008* (2006.01)
*G16H 10/60* (2018.01)

(52) U.S. Cl.
CPC .............. *A61F 9/008* (2013.01); *G16H 10/60* (2018.01); *A61F 2009/00876* (2013.01)

(58) Field of Classification Search
None
See application file for complete search history.

(56) References Cited

U.S. PATENT DOCUMENTS

| 6,306,127 | B2 | 10/2001 | Homer |
| 8,206,379 | B2 | 6/2012 | Homer |
| 9,931,171 | B1 * | 4/2018 | Peyman .................. A61B 3/14 |
| 10,744,034 | B2 | 8/2020 | Homer |
| 2003/0133596 | A1 * | 7/2003 | Brooks .................. G07C 9/37 382/115 |
| 2005/0049584 | A1 * | 3/2005 | Homer ................ A61F 9/00817 606/33 |
| 2008/0028247 | A1 * | 1/2008 | Muraoka ................ G06F 21/86 713/340 |

(Continued)

FOREIGN PATENT DOCUMENTS

| WO | 2001003569 | 8/2001 |
| WO | 2002062259 | 8/2002 |

OTHER PUBLICATIONS

"Iris pigmentation and pigmented lesions: an ultrastructural study," Trans Am Ophthalmol Soc 1988;86:581-687. PMID: 2979031; PMCID: PMC1298824.

(Continued)

*Primary Examiner* — Lynsey C Eiseman
(74) *Attorney, Agent, or Firm* — Perkins Coie LLP

(57) ABSTRACT

A system for altering the eye color of a patient with a color alteration procedure includes a laser system having a housing around at least one component of the laser system. The laser system also has a perimeter circuit configured to detect a breach of the housing based on the perimeter circuit being broken resulting in an electrical current flowing through the perimeter circuit being ceased or a change in resistance in the perimeter circuit. The system also includes software that detects, by the perimeter circuit, the breach based on the perimeter circuit being broken. The software also executes, based on the breach, an electronic lockout of the laser system such that the laser system cannot be operated without receipt of a command lifting the electronic lockout.

20 Claims, 8 Drawing Sheets

(56) References Cited

U.S. PATENT DOCUMENTS

| | | | | |
|---|---|---|---|---|
| 2016/0026829 A1* | 1/2016 | Brocker | .................. | G06F 21/87 |
| | | | | 726/34 |
| 2016/0089550 A1* | 3/2016 | DeBenedictis | ........ | A61B 18/20 |
| | | | | 601/3 |
| 2020/0064879 A1* | 2/2020 | Jawidzik | .................. | G05G 1/38 |
| 2020/0345431 A1* | 11/2020 | Patton | .................... | G06N 20/00 |

OTHER PUBLICATIONS

"Image-Based Modeling of the Human Eye" IEEE Transactions On Visualization And Computer Graphics, vol. 15, No. 5, Sep./Oct. 2009.

"Don't it make my blue eyes brown: heterochromia and other abnormalities of the iris" Eye (2012) 26, 29-50; Published online Oct. 7, 2011; Presented at the Oxford Ophthalmological Congress 2010.

"Scheimpflug Camera-Based Stereo-Digital Image Correlation for Full-Field 3D Deformation Measurement," Hindawi Journal of Sensors, vol. 2019, Article ID 5391827, 11 pages (Oct. 10, 2019), https://doi.org/10.1155/2019/539182.

"Introduction To OCT" http://obel.ee.uwa.edu.au/research/fundamentals/introduction-oct/ Date unknown, downloaded Nov. 9, 2020.

"American National Standard for Safe Use of Lasers," ANSI Z136.1-2007, ISBN-13: 978-0-912035.65-9 & ISBN-10: 0-912035-65-X, (May 2007).

"Development of Close Proximity Wireless Technology with Integrated On-Chip Antenna," https://www.renesas.com/us/en/about/press-room/development-close-proximity-wireless-technology-integrated-chip-antenna, Jun. 29, 2010.

\* cited by examiner

SYSTEMS AND METHODS FOR FOR PHYSICAL AND ELECTRONIC SECURITY OF MEDICAL DEVICES

RELATED APPLICATION(S)

This application claims priority to and the benefit of U.S. Provisional Application No. 63/165,687, filed Mar. 24, 2021, titled "Systems And Methods For Physical And Electronic Security Of Medical Devices," which is hereby incorporated by reference.

FIELD OF THE INVENTION

The invention relates to providing security and proper use of medical devices related to changing an eye color of a patient.

BACKGROUND

The use of lasers for eye surgery has increased recently. However, while laser eye surgery is a known option for the correction of one or more vision problems such as nearsightedness (myopia), farsightedness (hyperopia), and astigmatism, little interest has been shown to operations other than those for correcting vision problems. For example, advancements in laser eye surgeries have focused on operations through which a laser may reshape a patient's cornea and have ignored other parts of a patient's eye and procedures therefor.

SUMMARY

In view of this, methods and systems are discussed herein for delivering laser light to an iris of a patient. In particular, the methods and systems discussed herein are for performing an eye color changing procedure through this delivery of laser light. For example, changing a person's eye color may be performed by delivering laser light to portions of the eye that are responsible for giving the eye its color (e.g., the iris).

To achieve this effect, the methods and systems must overcome several technical hurdles. For example, as opposed to other types of eye treatments, color change procedure may require multiple procedures, the characteristics of which may be dependent on the patient and the number of previous procedures involving the patient. Additionally, as opposed to conventional treatments which are heavily influenced by manual adjustments of a physician, color change procedures are highly automated, and any one procedure may take only seconds to perform. Accordingly, ensuring that the settings of a laser system (e.g., power level, pattern to be followed, etc.) are correct and that the laser system is in proper working order, prior to beginning the procedure, is of critical importance. The methods and systems discussed herein therefore provide mechanisms for ensuring that the laser system the correct procedural settings are used, the patient is being applied on the correct patient, and/or the laser system is in proper working order.

In view of these technical hurdles, the systems and methods discussed herein provide for the acquiring of iris or retinal scans before a treatment. The scans may be compared by the system to determine the patient's identity. The system may display a confirmed identity and enable a laser system to deliver laser light for the color alteration procedure. Also, a laser system is provided with a perimeter circuit which, when broken, causes an electronic lockout of the laser system. Similarly, a laser system may incorporate a sensor to detect motion of the laser system or determine a location of the laser system such that if either is improper, an electronic lockout be executed.

These methods and systems provide numerous advantages over conventional methods for securing medical devices, particularly in the field of laser treatment for eyes. For example, securing the disclosed laser systems utilizing electronic lockouts provides an effective, yet reversible, way to control access to, and proper functioning of, the laser system. Similarly, verifying the patient's identity before treatment is delivered ensures that not only is the correct patient being treated but also that the correct treatment is being given. Determining the location or movement of the laser system may also ensure that the device is being used in the proper way and at the proper location. Prior art devices lacking such features are at increased risk of being used improperly.

In one aspect, a system for altering the eye color of a patient with a color alteration procedure includes a laser system having a housing around at least one component of the laser system. The laser system also has a perimeter circuit configured to detect a breach of the housing based on the perimeter circuit being broken resulting in an electrical current flowing through the perimeter circuit being ceased or a change in resistance in the perimeter circuit. The system also includes software that detects, by the perimeter circuit, the breach based on the perimeter circuit being broken. The software also executes, based on the breach, an electronic lockout of the laser system such that the laser system cannot be operated without receipt of a command lifting the electronic lockout.

In another interrelated aspect, a tangible, non-transitory, machine-readable medium storing instructions that, when executed by a data processing apparatus, causes the data processing apparatus to perform operations comprising those of any of the above method embodiments.

In yet another interrelated aspect, a system may include one or more processors and memory storing instructions that, when executed by the processors, cause the processors to effectuate operations comprising those of any of the above method embodiments.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification, "a portion" refers to a part of, or the entirety of (i.e., the entire portion), a given item (e.g., data) unless the context clearly dictates otherwise.

DETAILED DESCRIPTION OF THE DRAWINGS

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention.

The present disclosure provides improved methods and systems for the security and proper use of medical devices (e.g., the disclosed laser systems) for changing the eye color of a patient. For example, a reference scan of a patient's iris or retina may be captured and compared with a second scan later in time to determine the identity of the patient. Immediately before treatment, for example, confirmation of the identity may be displayed at a user interface and the laser system may be enabled for delivering treatment. To facilitate a laser system being secure (e.g., not tampered with) such systems may include a perimeter circuit that is configured to detect a breach of the laser systems housing. This may be done by a perimeter circuit being broken or a change in a major resistance in the perimeter circuit. If the perimeter circuit is broken, the system may execute an electronic lockout to prevent the delivery of laser energy. Also, a sensor may be incorporated into the laser system that may detect improper movement or an improper location of the laser system. If detected, the system may again execute an electronic lockout to prevent the delivery of laser energy.

Figure 1:
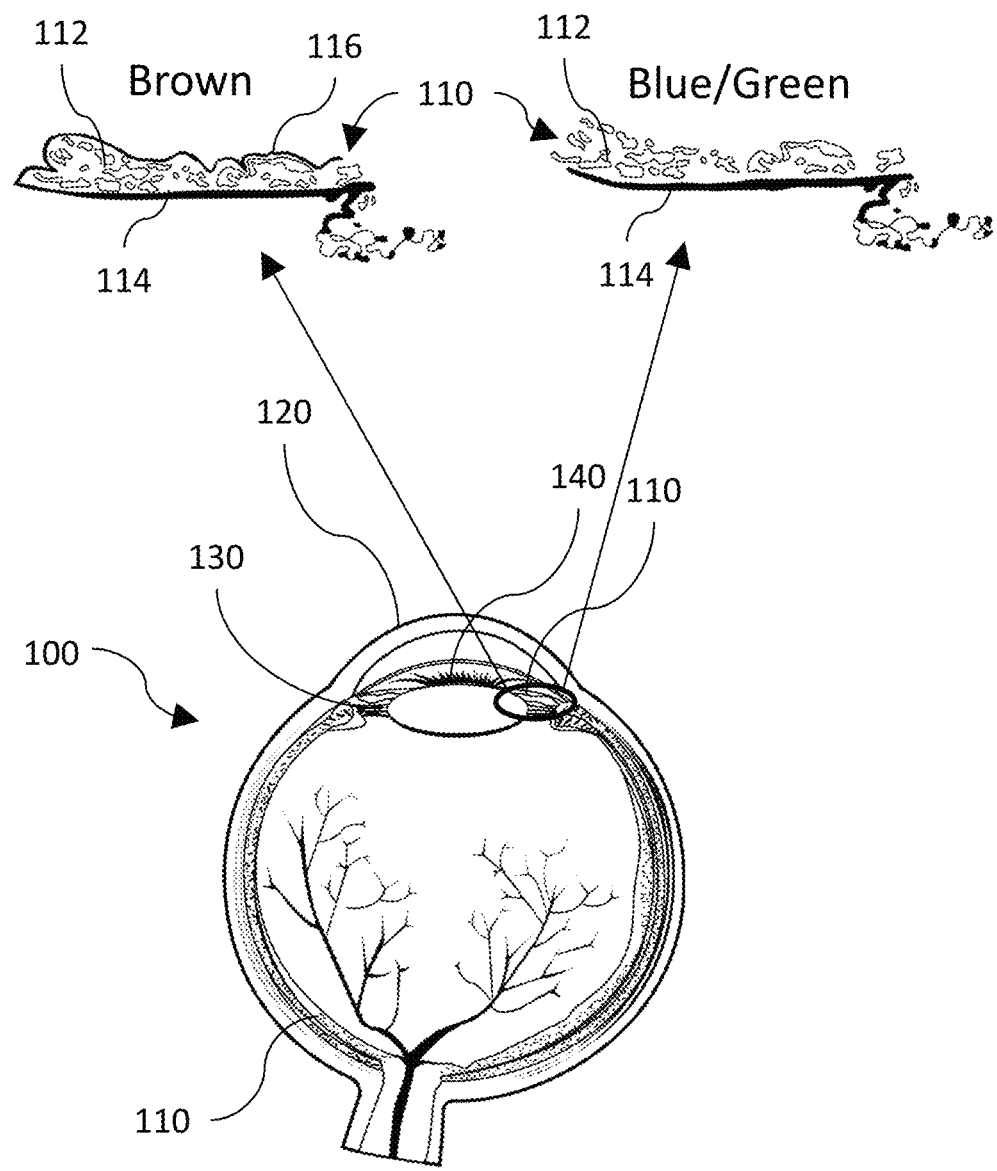
FIG. 1 shows a simplified diagram of the eye and iris.

Before describing the color alteration procedure, which is applicable to many embodiments of the present disclosure, a brief overview of the anatomy of the eye is provided. As shown in FIG. 1, eye 100 is composed of several anatomical structures, a few of which are discussed below. Central to the present disclosure, the iris 110 is responsible for the color of the eye. Other portions of the eye include, for example, cornea 120, lens 130, pupil 140, and retina 150. While care should be taken to avoid damaging any part of the eye, in the practice of laser safety, special precautions should be taken to avoid directing unwanted laser light through the pupil and into the lens as this part of the eye naturally focuses light onto the retina. Such focusing of already intense laser light may result in injury to the retinal nerves.

Shown in the insets above the eye are two examples of irises. The example on the left is a depiction of an iris 110 in a person with brown eyes. The example on the right depicts an iris 110 of a person with blue or green eyes. The perceived color is due to light reaching the eye being separated into its component wavelengths by stromal fibers in the middle region of the iris—referred to as the iris stroma 112. The separation is similar to the separation exhibited when light passes through a prism. In both cases, the iris has a posterior surface 114 that contains a fairly thick (several cells deep) layer of pigmentation that primarily absorbs visible light wavelengths longer than blue or green. However, in the example on the left for a person with brown eyes, there is an additional anterior surface that contains brown pigment, herein referred to as "stromal pigment" 116. The brown stromal pigment gives the eye a brown color. Eyes without the stromal pigment reflect mostly blue or green light as described above, giving the eye a blue or green color.

A brief summary of a color alteration procedure as referenced herein is provided. Laser light may be delivered to the stromal pigment to cause an increase in temperature of the stromal pigment. This process may be repeated several times to repeatedly raise and lower the temperature of the stromal pigment. This raising and lowering of the temperature causes the body to deploy macrophages (part of the body's natural immune response) to the stromal layer. These macrophages then remove a portion of the stromal pigment responsible for giving the eye its brown color. Repeated procedures may be performed to provide varying degrees of color change to make the eye appear a deeper blue/green. The delivery of the laser light may be in a scanning pattern (e.g., a spiral pattern surrounding the pupil or a raster pattern avoiding the pupil) to deliver the treatment to the entire iris.

Figure 2:
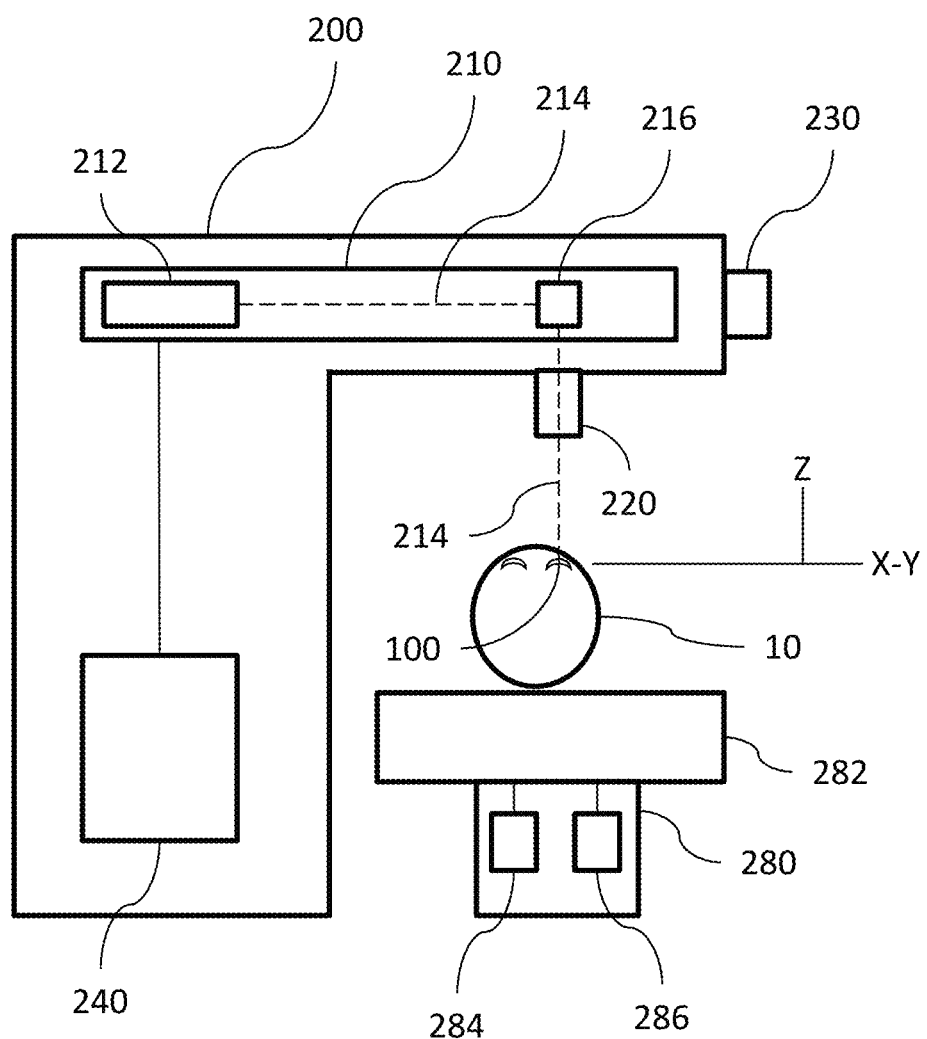
FIG. 2 shows a simplified diagram of a laser system and patient positioning system in accordance with one or more embodiments.

FIG. 2 shows a simplified diagram of a laser system and patient positioning system in accordance with one or more embodiments. One embodiment of the overall system 200 may include the laser system 210 and a patient positioning system 280. The head of patient 10 (with eyes 100) is shown supported by the patient positioning system in a location suitable for the color alteration procedure. The laser system may include the laser head 212 which provides laser light 214. The laser head may include components to generate laser light at varying wavelengths, for example, at 1064 nm or 532 nm (Nd:YLF or Nd:YAG). Exemplary pulse widths may be in the 5-300 ns with repetition rates of 5-300 kHz and an $M^2 \leq 1.2$.

The laser head may include an energy source (aka a pump or pump source), a gain medium, and two or more mirrors that form an optical resonator. Exemplary energy sources include: electrical discharges; flashlamps; arc lamps; output from another laser; and chemical reactions. Exemplary gain media include: liquids (e.g., dyes comprising chemical solvents and chemical dyes); gases (e.g., carbon dioxide, argon, krypton, and helium-neon); solids (e.g., crystals and glasses, such as yttrium-aluminum garnet, yttrium lithium fluoride, sapphire, titanium-sapphire, lithium strontium aluminum fluoride, yttrium lithium fluoride, neodymium glass, and erbium glass), which may be doped with an impurity (e.g., chromium, neodymium, erbium, or titanium ions) and may be pumped by flashlamps or output from another laser; and semiconductors, with uniform or differing dopant distribution (e.g., laser diode).

Embodiments of the laser head may include an optical frequency multiplier (e.g., a frequency doubler and sum-frequency generator), where the laser output frequency is increased by passing it through a non-linear crystal or other material. The benefit of an optical frequency multiplier is that it increases the range of frequencies/wavelengths available from a given gain medium. The non-linear material may be inserted into the optical resonator for one-step frequency multiplication, or the fundamental (i.e. non-multiplied) output beam may be passed through the non-linear material after leaving the optical resonator for two-step frequency multiplication. Exemplary non-linear materials for frequency doubling may include: lithium niobate, lithium tantalate, potassium titanyl phosphate, or lithium triborate. Two-step frequency tripling is typically performed by frequency doubling a fraction of the fundamental output beam in a first step. The doubled fraction of the fundamental beam and the non-doubled remainder of the fundamental beam are then coupled into a second non-linear frequency tripling material in a second step for sum-frequency mixing. Exemplary non-linear materials for frequency tripling may include potassium dihydrogen phosphate.

One combination of gain medium and optical frequency multiplier is Nd:YAG with a frequency doubler. The natural harmonic of a laser beam generated by an Nd:YAG gain medium is a wavelength of 1,064 nm, which is then halved to 532 nm by the frequency doubler. This wavelength may be utilized as: (a) it falls within the visible light spectrum (i.e., green), thereby passing through the clear cornea with little or no absorption; (b) it has a high absorption coefficient in stromal pigment, thereby effecting selective photothermolysis in the anterior stromal pigment of the iris; and (c) the wavelength is relatively short, thereby limiting the depth of penetration and avoiding unwanted damage to the IPE. Any other combination of gain media and optical frequency multiplication that meets these three criteria is also may also be implemented in some embodiments.

Laser pulse widths may be in the nanosecond range (i.e., from below 1 nanosecond to 1 microsecond) and the pulse repetition rate may be in the kilohertz range (i.e., from below 1 kHz to 1 MHz). Some embodiments may have a pulse width between 5 ns and 300 ns, which may provide improved pigment denaturation. Q-switching may be utilized as a preferred pulsing method as it tends to be optimally suited to the nanosecond pulse width. Some embodiments include active Q-switching with a modulator device.

As used herein, "laser" means any device capable of generating a beam of optical radiation, whether in the infrared, visible light, or ultraviolet light spectrum. The term "laser" is not intended to restrict: (a) the properties of the optical radiation in terms of monochromaticity or coherence (e.g., divergence or directionality); (b) whether the radiation is continuous or pulsed; (c) if pulsed, the specific pulse width (e.g., zeptosecond attosecond, femtosecond, picosecond, nanosecond, millisecond, or microsecond); (d) the repetition rate; (e) the laser power; (f) the wavelength or frequency of the beam; (g) the number of wavelengths or frequencies, i.e., single v. multi-frequency output (e.g., intense pulsed light); (h) the number of beams, i.e., single v. multiple beams (e.g., splitting of a single beam or generating multiple beams from multiple lasers); or (i) the gain medium.

As used herein, "laser power" may mean either $W/cm^2$ or $J/cm^2$, depending on the context—as they are related by the exposure time. The MPE may be expressed in either of those units. For example, MPE may include the maximum level of laser radiation to which a fundus may be exposed without hazardous effects or biological changes in the eye.

Accordingly, when the specification refers to a laser power in terms of an MPE, the exact value of the laser power depends on, among other things, the beam spot size, pulse duration, or wavelength, and whether the laser is pulsed or continuous, etc. Thus, the determination of the MPE provides a basis for the skilled person to determine the laser power in the various embodiments disclosed herein.

As used herein, when referring to "reducing," "lowering," "less," etc., in the context of adjusting the laser power, this is understood to mean that the laser system may reduce the laser power from a current value to a lower (nonzero) value while still delivering laser light in some respect. These definitions also include redirecting the laser beam (e.g., to a beam dump) such that the delivered laser power is reduced. These definitions also include turning off the laser system (i.e., lowering the laser power to zero). Lastly, reducing the laser power may also include performing any of the above in a repetitive fashion thereby lowering the duty cycle of the laser beam or performing any combination of the above in an intermittent fashion.

Galvos systems 216 (also referred to as the x-y beam guidance system) may be included in the laser system and may include adjustable mirrors to provide a means of delivering the laser light to various locations on an X-Y plane (typically the plane of the iris where the laser light usually focused). Further implementations of the laser system may include, for example rangefinders and/or optical tracking systems, which may include cameras to determine an X-Y deviation of the center of the eye relative to the optical axis of the laser system.

In some embodiments, the x-y beam guidance system may scan the beam spot about the iris surface. The scanning parameters may include the size, shape, and position of the target region, the line and spot separation between each beam spot, and the predetermined scan pattern. The computer imaging software may determine the size, shape, and position of the target region based upon iris images captured by the x-y imaging system and transmitted to the computer for processing. Once processed, the size, shape, and position data may be transmitted to the scanning program to drive the x-y beam guidance system. New iris images may be captured at predetermined intervals and transmitted to the computer for processing throughout the procedure. Captured images are compared, and if they indicate a change in iris position, the computer imaging software calculates the x-y deltas and transmits the shift coordinates to the scanning program, which in turn executes the shift in the scanning position. In some procedures, a topical cholinergic agonist such as pilocarpine hydrochloride ophthalmic solution 2% (e.g., Isopto Carpine 2% from Alcon, Geneva, Switzerland) may be instilled in the target eye prior to treatment to constrict the pupil, flatten out the iris surface, and mitigate changes in the iris size and shape during the procedure. The line and spot separation between each beam spot may be predetermined and programmed into the scanning program prior to treatment. In some cases, the spot and line separation place each beam spot tangent to the others throughout the target region. The scan pattern may be raster (including slow-x/fast-y and slow-y/fast-x), spiral (including limbus to pupil and pupil to limbus), vector, and Lissajous scans.

In one embodiment, the x-y beam guidance system may scan the beam spot about the iris surface by means of controlled deflection of the laser beam. Embodiments utilizing beam steering in two dimensions may drive the beam spot about the two-dimensional surface of the iris. Beam motion may be periodic (e.g., as in barcode scanners and resonant galvanometer scanners) or freely addressable (e.g., as in servo-controlled galvanometer scanners). Exemplary beam steering in two dimensions may include: rotating one mirror along two axes (e.g., one mirror scans in one dimension along one row and then shifts to scan in one dimension along an adjacent); and reflecting the laser beam onto two closely spaced mirrors mounted on orthogonal axes.

There are numerous methods for controlled beam deflection, both mechanical and non-mechanical. Exemplary non-mechanical methods may include: steerable electro-evanescent optical refractor or SEEOR; electro-optical beam modulation; and acousto-optic beam deflection. Exemplary mechanical methods may include: nanopositioning using a piezo-translation stage; the micro-electromechanical system or MEMS controllable microlens array; and controlled deflection devices. Mechanically controlled deflection devices may include: motion controllers (e.g., motors, galvanometers, piezoelectric actuators, and magnetostrictive actuators); optical elements (e.g., mirrors, lenses, and prisms), affixed to motion controllers; and driver boards (aka servos) or similar devices to manage the motion controllers. The optical elements may have a variety of sizes, thicknesses, surface qualities, shapes, and optical coatings, the selection of which depends upon the beam diameter, wavelength, power, target region size and shape, and speed requirements. Some embodiments may utilize optical elements that are flat or polygonal mirrors. An embodiment of the motion controller may include a galvanometer, including a rotor and stator (to manage torque efficiency) and a position detector (PD) (to manage system performance). An exemplary PD may include one or more illumination diodes, masks, and photodetectors. Driver boards may be analog or digital. Scan motion control might also comprise one or more rotary encoders and control electronics that provide the suitable electric current to the motion controller to achieve a desired angle or phase. The installed scanning program disclosed above may be configured to collect measured scan and target region data.

The x-y beam guidance system may apply the laser spot to all or any portion of the anterior iris surface. Treated fractions of the anterior iris surface may include the following (which are inclusive and do not take into account any spared tissue due to line and/or spot separations): greater than ¼; greater than 30%; greater than ¼; greater than ½; and greater than ¾.

The system can include one or types of rangefinding apparatuses to measure the Z distance from a reference point to the target (e.g., the iris surface). As used herein, the Z direction is taken to be the vertical direction, perpendicular to the X-Y plane (e.g., the iris surface). A component referred to herein as optical exit 220 may be provided to allow the exiting of laser light to reach the eye. Optical exit 220 may include windows, lenses (e.g., dichroic lenses), mirrors, shutters, or other optical components. In some implementations, the system may include platform control 230, which may be configured to provide coarse adjustment (manually or automatic computer-controlled) in the X, Y, or Z directions. The platform control 230 may also be configured to perform fine adjustments similar to the above, with such fine adjustments implemented by computer control. Also included in some implementations are control computer and power supplies, depicted by element 240 in FIG. 1. Alternatively, control computers or electronics and some or all of the needed power supplies need not be contained in the system 200 as depicted in FIG. 1, but may be distributed in other locations or networked to be operatively connected to the laser system. Examples of rangefinding apparatuses may include systems that perform triangulation, time-of-flight measurements, etc., with one specific example being an optical coherence tomography system. Further discussion of rangefinding and/or tracking apparatuses is provide throughout the application.

Patient positioning system 280 is shown in the simplified diagram as containing patient support 282. Examples of patient support may include a flatbed, recliner, couch, head or neck brace, etc. Control of the patient positioning system may be realized by, for example, X-Y actuator 284 and/or Z actuator 286, which may be configured to move the patient in the respective directions for optimal alignment with the delivered laser light.

Figure 3:
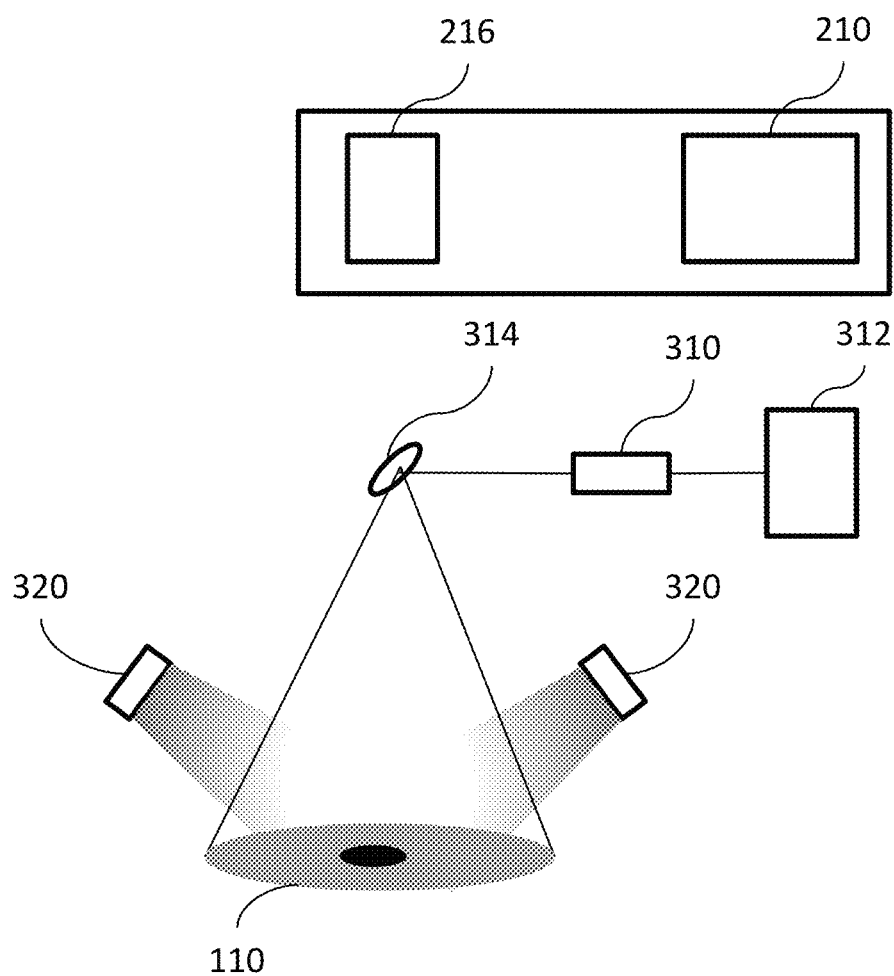
FIG. 3 shows a simplified illustration of a laser system that includes an image sensor in accordance with one or more embodiments.

FIG. 3 shows a simplified diagram of a laser system 210 and image sensor 310 for use in mapping the iris in accordance with one or more embodiments. Determination of the proper laser power may depend on variations in the absorption of the delivered laser power due to inhomogeneities in regions 330, 332, 334 of the stromal pigment layer. Such variations may be caused by, for example, varying density of the stromal pigment, varying sizes of stromal pigment cells, types and compositions of the stromal pigment, etc. As such, regions of the iris where the stromal pigment has a higher absorption coefficient reach a higher temperature (or a target temperature faster) for a given laser power. These differences, if not accounted for, may result in uneven color alteration or possibly even damage to the eye. To address this problem, some implementations of the disclosed methods may include imaging the iris with an image sensor operatively connected to a computer 312 prior to the procedure to generate images of the iris. Examples of image sensors may include a CCD, COMS, or camera used in conjunction with an illumination source 320, wherein the wavelength range of the sensor includes the wavelength of the illumination source. Exemplary wavelengths include near and mid-infrared, visible light, or the specific wavelength of the treatment laser beam. An embodiment might also include software programs capable of creating a digital color model from the captured images and mapping or otherwise analyzing the stromal pigment coefficients for the treatment wavelength based on the model. Exemplary digital color models include RGB (which stands for red-green-blue), HSI (for hue-saturation-intensity), HSL (for hue-saturation-lightness), HSV (for hue-saturation-value), CMY (for cyan-magenta-yellow), and YIQ (luminance-inphase-quadrature).

To facilitate integration of the image sensor with existing laser system, the image sensor may incorporate a dichroic optic 314 (e.g., a dichroic lens, mirror, or prism) to divert incoming light reflected from the iris the reflective or refractive side of the optic and directing it to the image sensor, while allowing outgoing laser light to pass through the optic to the iris surface for treatment. Such implementations have the advantage that the light may be collected on the same optical axis as the laser system. This has the advantage of both simplifying and making more accurate the generation of scans relative to the geometry of laser system because it avoids the need to account for an off-axis image sensor.

Figure 4:
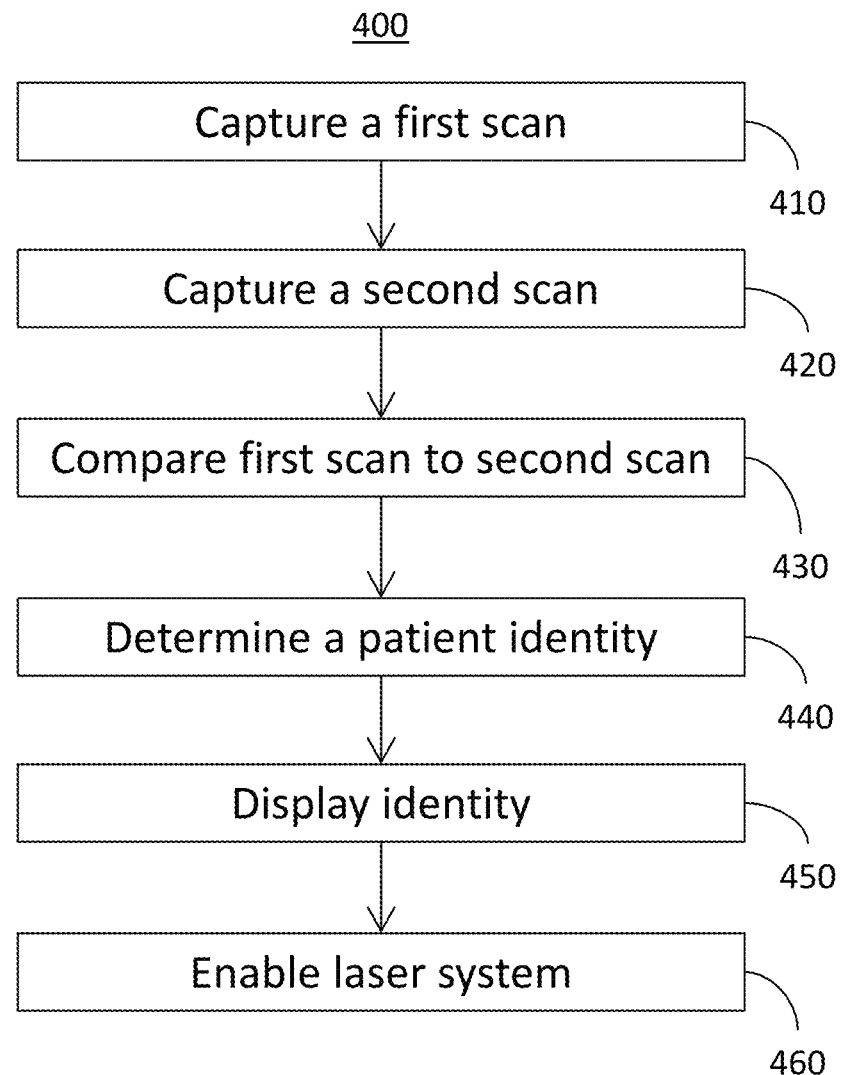
FIG. 4 shows a process for allowing the eye color changing procedure to be performed by a laser system in accordance with one or more embodiments.

FIG. 4 shows a process for allowing the eye color changing procedure to be performed by a laser system in accordance with one or more embodiments. As described with reference to FIG. 3, in some embodiments the system may also include an image sensor to capture a scan of the patient's iris or retina. Such scans may be utilized to ensure patient identity and/or a proper medical condition prior to the end of an eye color alteration procedure. For example, process 400 (e.g., via one or more components of FIG. 2, 3, or 5-7) may represent the steps taken by one or more devices as shown in FIG. 2, 3, or 5-7 when performing an eye color changing procedure.

At step 410, process 400 may (e.g., via one or more components of FIG. 2, 3, or 5-7) capture a first scan. For example, an image sensor may capture the first scan at a first time prior to the altering of the eye color. The first scan may be of at least one of an iris or retina of the patient. In some implementations, the first scan may be part of a confirmed identity, such as what might occur during patient onboarding. The confirmation can include associating it with other patient information such as official identifying numbers, other biometrics such as fingerprints, medical records, etc.

At step 420, process 400 may (e.g., via one or more components of FIG. 2, 3, or 5-7) capture a second scan. For example, the second scan may be captured with the image sensor and at a second time later than the first time and prior to the altering of the eye color, the second scan being of at least one of the iris or the retina of the patient. In some implementations, the first scan may be done as part of a consultation exam or other pre-procedure scan. The second scan may, for example, be taken shortly before the procedure or even at the start of the procedure to confirm the identity of the patient as described in the next steps.

At step 430, process 400 may (e.g., via one or more components of FIG. 2, 3, or 5-7) compare the first scan captured at the first time with the second scan captured at the second time. The second time may be later than the first time and may be prior to the altering of the eye color. In some embodiments, the second scan may also be at least one of the iris or the retina of the patient. Software as described in FIG. 7 may perform the comparison. For example, machine learning algorithms may be trained from a patient library of iris patterns and/or retinal patterns (e.g., which may contain the first scan) to recognize the anatomical patterns in the eye of a particular patient.

At step 440, process 400 may (e.g., via one or more components of FIG. 2, 3, or 5-7) determine an identity of the patient. For example, the identity may be determined based on matching the first scan captured at the first time with the second scan captured at the second time.

For embodiments utilizing retinal scanning, the scans may map patterns of the patient's retina. Blood vessels in the retina absorb light better than the surrounding tissue and thus are readily identifiable with suitable lighting. For example, a retinal scan may include the system projecting low-energy infrared light into the eye via an infrared light source (e.g., infrared illumination source 320 or possibly a different illumination source having a more focused beam). The system may then control the source to direct the light to trace out a path on the retina. Due to variations in the absorbency of the light caused by retinal blood vessels, the amount of light reflected varies during the scan. The scan patterns may be stored in a database (e.g., a first pattern to establish a baseline). The scan patterns may also be compared with patterns already stored in the database (e.g., a second pattern to confirm the identity).

For embodiments utilizing iris scanning, the scan may include the system acquiring video or still images of the iris that contain information about the significantly complex and random-seeming patterns in the iris (e.g., such as due to the presence or absence of stromal pigment fibers). Comparisons of these patterns with prior patterns may be performed in a manner similar to those done with retinal scans. In the context of the present application (color alteration via removal of stromal pigment), additional considerations may apply to some iris scans. Specifically, the goal of the procedure is to alter the iris to change its color. Therefore, this necessarily alters the iris pattern that may be used for identification. As such, in some embodiments, after a procedure (and optionally significantly after the procedure such as when macrophagic removal of the stromal pigment has significantly concluded for the given stage of treatment) the system may obtain a new iris scan to serve as a baseline for the patient identity. It would be this new baseline that the system may compare to the second scan which occurs immediately prior to the next treatment.

In some embodiments, returning to the example of utilizing machine learning algorithms for scan comparison, the trained algorithm described above may use the second scan as input and determine the identity of the patient and/or a confidence value of a match.

At step 450, process 400 may (e.g., via one or more components of FIG. 2, 3, or 6-7) display a confirmation of the identity. For example, the system may generate, for display on a user interface, the confirmation of the identity of the patient. The confirmation may be in the form of graphical and/or textual output at the display. The confirmation may include, for example, a patient's name, medical record number, or other personal identifying information.

In some embodiments, the system may display at a console (e.g., a physician console, technician console, or other console associated with the laser system) the patient medical record data based on the iris or retina scan. The patient medical record data may be in the form of textual and/or graphical information representative of the patient's medical records. This may include, for example, the patient's current or past medical condition, information about past and/or the current color alteration procedure, etc. Accordingly, in some embodiments, the system may enable the laser system to deliver the treatment plan based on the first scan or the second scan corresponding to patient identification included with the patient medical record data. This may include the system automatically setting the laser power of the laser system based on the patient medical record patient treatment plan.

At step 460, process 400 may enable a laser system. For example, the enabling of the laser system may allow delivery of laser light by the laser system to the iris or retina of the patient upon confirmation of the identity. In some embodiments, enabling the laser system may include the reversing of electronic lockouts as described elsewhere herein. In some embodiments, the system may be configured to, and/or required to, receive user input in response to the confirmation to enable the delivery of the laser light. This additional step may thus require both the automated identity verification described above and an additional human action taken before the laser system is enabled. After the laser system is enabled, the process may further include the laser system delivering the laser light.

Figure 7:
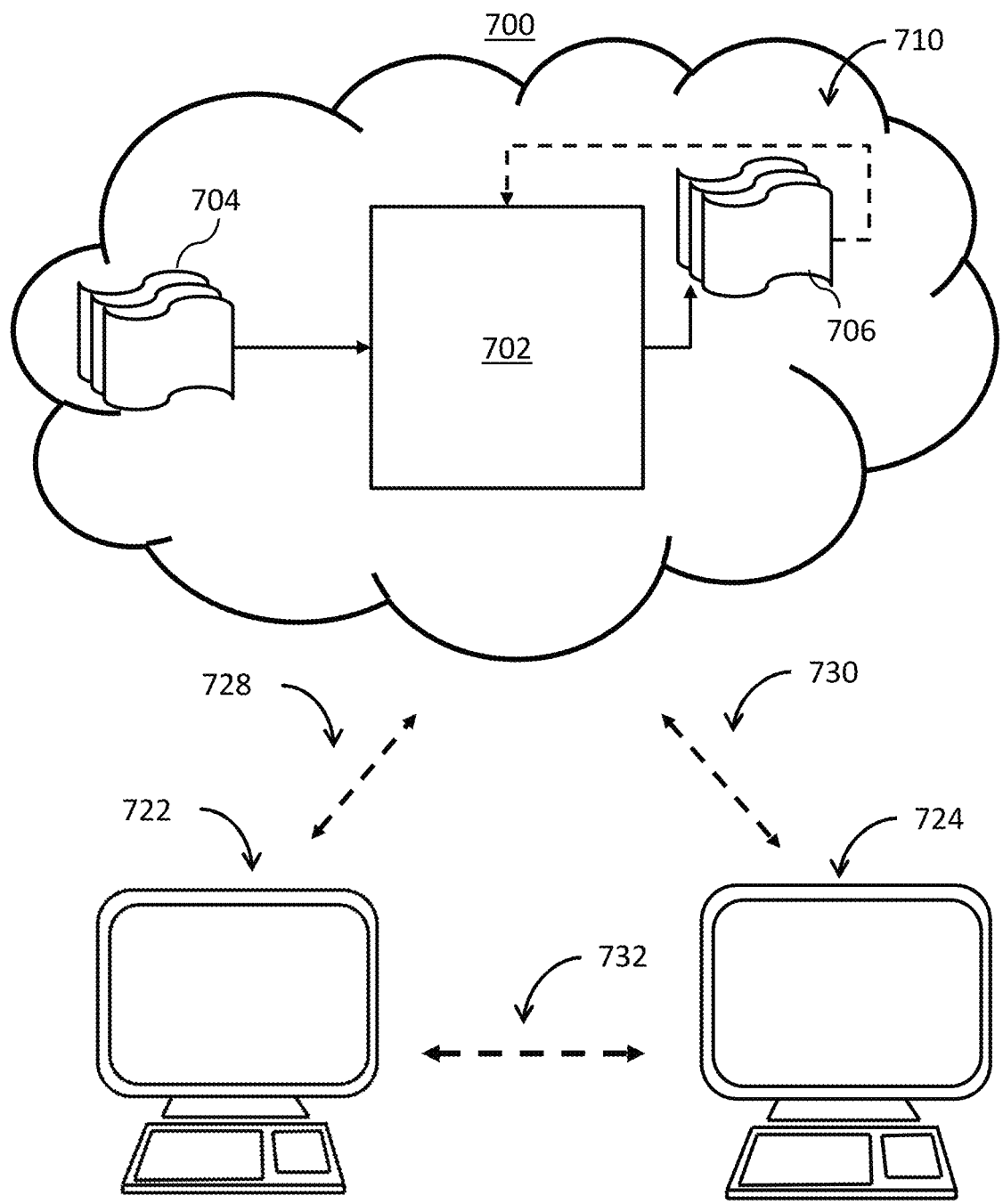
FIG. 7 shows an illustrative system for performing an eye color changing procedure in accordance with one or more embodiments.

In some embodiments, medical databases may be accessed via the networked computing systems disclosed in FIG. 7. With the confirmed identity, such access may be more readily obtained from secure medical record databases. In some embodiments, the patient medical record data may include a treatment plan for delivery by the laser system.

Figure 5:
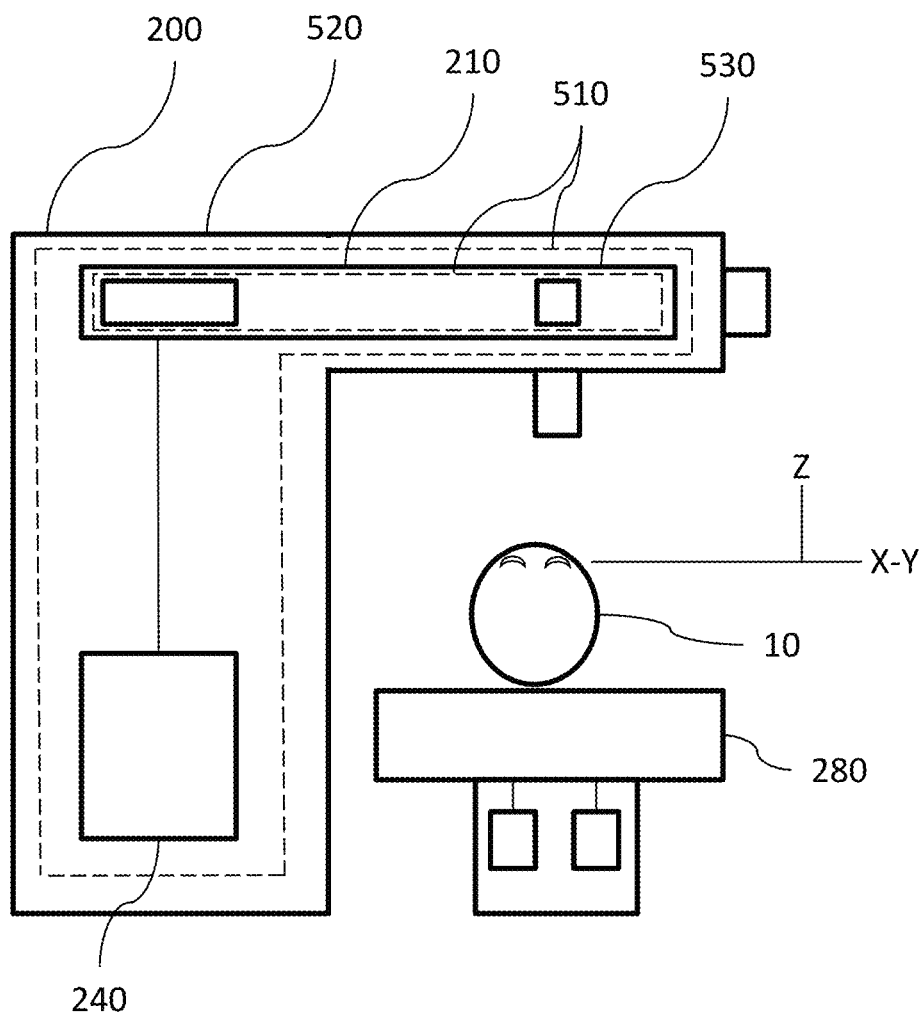
FIG. 5 shows an illustrative system that includes a perimeter circuit in accordance with one or more embodiments.

FIG. 5 shows an illustrative system that includes a perimeter circuit in accordance with one or more embodiments. In some implementations, various components of the system and (or the system itself) may be enclosed in housings. To provide enhanced security of the disclosed laser system 210 (or the broader system 200), one or more perimeter circuits 510 may be included that are capable of detecting a physical breach (e.g., through the housing) of the secured components and thus a potential unauthorized access. In some embodiments, there may be a housing around at least one component of the laser system. For example, there may be a system housing 520 surrounding a significant number of components of the system 200, such as laser system 210, computer 240, etc. In some embodiments, there may be housings around subcomponents, for example, a laser system housing 530 surrounding the laser system 210.

Associated with any housing in the system (e.g., system housing, laser system housing, etc.) the perimeter circuit may be configured to detect a breach of the housing based on the perimeter circuit being broken resulting in a ceasing of an electrical current flowing through the perimeter circuit or a change in resistance in the perimeter circuit. The above contemplates two exemplary ways in which the perimeter circuit may be embodied—as an actively energized circuit or as an un-energized circuit which may be tested as needed.

In embodiments where the perimeter circuit is energized, this may include having a current flowing through a contiguous conductor and some aspect of the current (e.g., a voltage, a current value, an impedance, etc.) may be monitored by an appropriate sensor (e.g., voltage detector, current detector, etc.) to detect or determine an impermissible change or cessation of the current. In some embodiments, the measured aspect may be compared to a threshold value before the system determines that a breach has occurred. To avoid false positives that may be due to normal fluctuations in the circuit, the measured aspect may need to fall below (e.g., 95%, 90%, 50%, etc.) of its nominal value. Accordingly, in an embodiment, the system may include a battery operatively connected to the perimeter circuit to energize the perimeter circuit. When the energy remaining in the battery is below a battery lockout threshold (e.g., 50%, 25%, 10%, 5%, etc.) the electronic lockout may execute as described herein. In some embodiments, the battery may be connected to the system such that under normal operation main power energizes the perimeter circuit. However, in the event that main power is interrupted the battery energizes the circuit to maintain the energization of the perimeter circuit for breach detection. This backup battery embodiment may also have a similar battery lockout threshold as described above.

In embodiments where the perimeter circuit is not normally energized, this may include having a similar perimeter circuit as described above, but without active monitoring of the circuit. When it is desired to test the perimeter circuit, the perimeter circuit may be energized via, for example, external main power (such as from a 120V/240V/360V supply), an internal or external battery, or by a power supply associated with the detecting device (e.g., power as supplied by a current detector or ohmmeter).

Examples of perimeter circuits may include, for example, a circuit completed via a metallic screw—either a screw head connecting adjacent terminal ends of a conductor or the body of the screw having physical contact with conductors at different locations along the length of the screw. For example, one portion of the perimeter circuit the configured to be at a more outer location and thus when the screw is engaged in outer portion of the screw contacts the conductor. And inner location of the conductor may then make similar contact with a more inner portion of the screw in such a way that the screw completes the circuit. Another example perimeter circuit may include one with electrical contacts that are in place such as when the housing is securely closed. For example, there may be an access plate that contains part of the perimeter circuit. When the access plate is in place, contacts on the access plate are connected with contacts on another part of the perimeter circuit on a nonremovable portion of the housing to complete the circuit. In yet another embodiment, the perimeter circuit may be a breakable conductive wire that is designed to break in the event of a breach such that even if the breach is repaired, the wire is still broken and thus evidences that a breach occurred (via the circuit made by the breakable wire being permanently interrupted). It is contemplated that there may be any number of perimeter circuits in any of the embodiments disclosed herein. Also, no limitation is ascribed to the shape of the perimeter circuit as the shape of such circuits may take an irregular shape and even not necessarily form a closed perimeter in a simple geometric sense as depicted by the simplified example in FIG. 5. For example, if the laser system housing was substantially cylindrical, one implementation of a perimeter circuit could be a spiral winding around the exterior of the housing with the terminal ends of the spiral connected and any number of electrical contacts being present along the length of the spiral to detect a breach as described above. As such, variations on the designs of the perimeter circuit are contemplated such that they may perform substantially the same functions disclosed herein. Also, while some embodiments include a perimeter circuit which may generally enclose a housing, the present disclosure also contemplates that a "perimeter circuit" may be any circuit which may be broken as described herein. For example, the perimeter circuit need not surround a "perimeter" of a component or housing and may, for example, merely have a portion of the circuit be fastened to an openable portion (or any other part) of a housing or other component such that opening or breaching of such may break the circuit. In some embodiments, one or more motion sensors may be located inside the housing. Such motion sensors may be configured to detect movement inside the housing in the event that the perimeter is breached and may provide redundancy to the perimeter circuit. The motion sensors may be operatively connected to the system to initiate an alert in a manner similar to the other security embodiments disclosed herein.

The electronic lockout of the laser system may be utilized to, either temporarily or permanently, prevent the laser system from delivering laser energy to a patient. The present disclosure contemplates numerous embodiments for doing so. In some embodiments, in response to a breach, the system may execute an electronic lockout of the laser system such that the laser system cannot be operated without receipt of a command lifting the electronic lockout. For example, in software there may be a password or code required for entry before the lockout is removed. To cause the lockout, some embodiments may include the system disabling the laser system by controlling a Pockels cell of the laser system to stop or reduce laser power output by the laser system. For example, the voltage applied to the crystal in a Pockels cell may be eliminated or changed to a value such that the laser power output drops to a very low fraction (e.g., 10%, 5%, 1%, etc.) of its nominal output or the power output is completely eliminated. In some embodiments, the electronic lockout may include locking out a control system of the laser system to prevent at least one command being accepted that is required for operation of the laser system. For example, under normal operation, the control system may require an operator to push a button (e.g. via a graphical user interface) to initiate treatment. The electronic lockout may disable the button such that a press at the graphical user interface is not recognized. As another example, the operator may be able to enter the necessary command, but the control system will not accept the command due to the lockout. In some embodiments, the system may electronically notify a third party of the detection, such as by sending an e-mail, automated call, log with the time(s)/place(s) of the detection, etc.

In some embodiments, the system may execute the electronic lockout by deleting of a configuration file necessary for operation of the laser system. For example, the laser system may require a configuration file, which may be in the form of a text or other data file that provides data needed by the laser system to perform the treatment. Such data may include the laser power, movement of the galvos to execute a scanning pattern, a location to focus the beam, the position of the patient's eye, etc. Such a configuration file may be unique to each patient due to their unique treatment parameters.

In some embodiments, lockout functionality may already be inherently present in the system and such may be utilized in any of the embodiments described herein. For example, the laser system may have a number of sensors or other detectors configured to detect conditions that would trigger a software interrupt. Such interrupts may be triggered by, for example, an energy sensor (e.g., pyroelectric or photodiode) placed in the beam path (or in receipt of a split off portion of the beam) such that under normal operations, if the energy sensor detected an unacceptable reading, initiates an interrupt that prevents laser output, prevents a warm-up protocol from initiating, etc. Embodiments of such energy sensors or other detectors may be at any point along the laser system such as proximate to the laser head, proximate to the galvos, or proximate to the last optic. Other pre-existing interrupts that may be utilized may include interrupts on power supplies, power modulators, etc.

In some embodiments, the system can be configured to allow for a restart once appropriately authorized or the physical system restored. For example, after a perimeter circuit is re-established, the system may permit normal functioning. As another example, after a lockout due to impermissible motion, a properly authorized administrator override/reset may be performed to return the system to operation.

Figure 6:
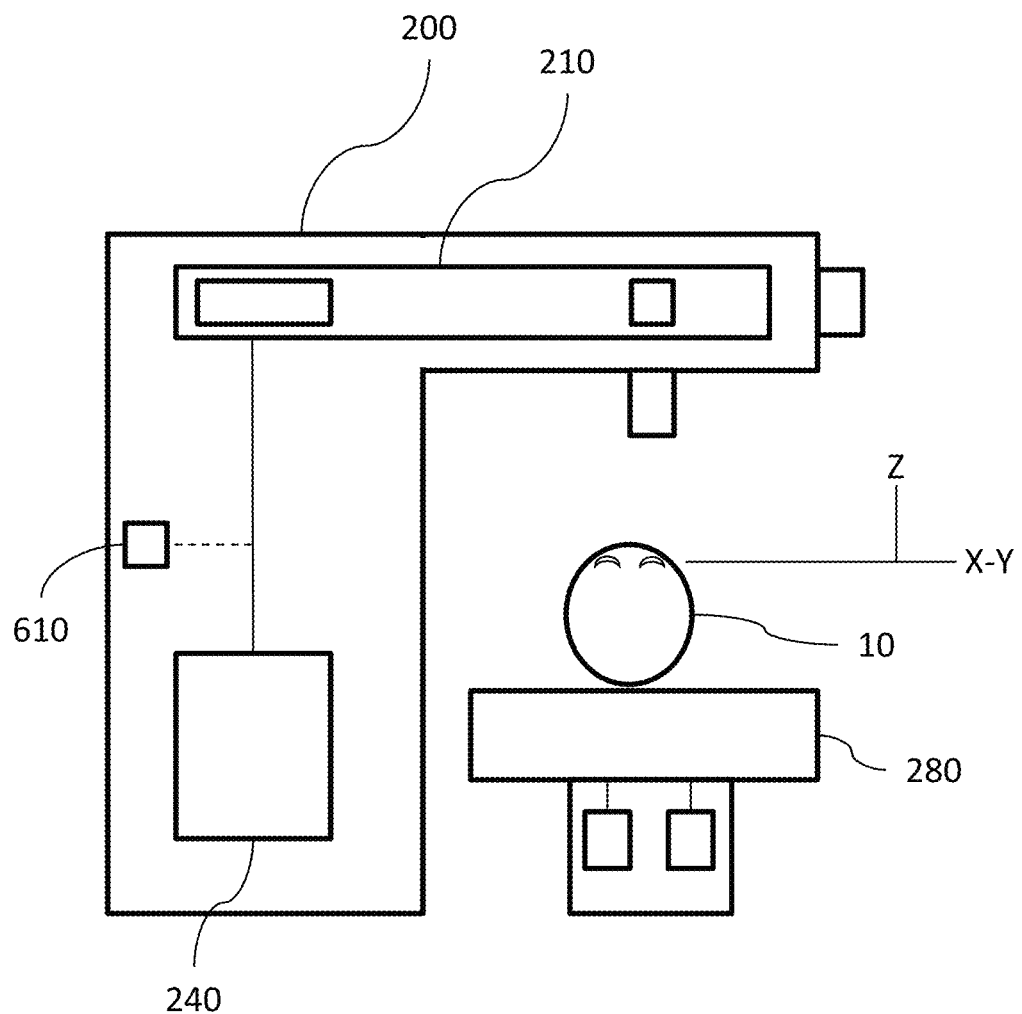
FIG. 6 shows an illustrative system incorporating a sensor for use in executing electronic lockouts in accordance with one or more embodiments.

FIG. 6 shows an illustrative system 200 incorporating a sensor 610 for use in executing electronic lockouts in accordance with one or more embodiments. In some embodiments, the disclosed systems may include one or more sensors that detect conditions of the laser system 210 that may cause the execution of an electronic lockout, in any of the ways described herein. For example, the system may include a sensor configured to detect movement or determine a location of the laser system. Software in the system may then detect, utilizing data from the sensor, a condition such as unacceptable movement or an unacceptable location that causes the laser system to execute an electronic lockout. The electronic lockout of the laser system may be executed such that the laser system cannot be operated without receipt of a command lifting the electronic lockout.

Embodiments of the sensor may be located at any location in or on the disclosed systems, for example, inside a housing, attached to a housing, attached to a component such as a computer, laser head, etc. Sensor 610 may be connected to computer 240 as shown, but in other embodiments may be wired or wirelessly in communication with a computer remote from the depicted system, which in turn may be in communication with the system 200 to cause the electronic lockout.

Some embodiments of the system may be configured such that the condition for lockout is some amount of movement of the laser system. Accordingly, the system may determine the movement and the electronic lockout may be executed based on the movement. For example, the sensor may be configured to detect movement comprising lateral movement, vertical movement, or tilting about any axis. In other embodiments, the sensor may be configured to detect movement comprising vibrations. While vibrations may comprise combinations of lateral movement, vertical movement, or tilting, in some embodiments, detection of vibrational movement may be distinct from other types of movement in that the system generally does not move from one place to another. Examples of physical sensors that may be utilized include a gyroscope or mercury switch. In some embodiments, the system may electronically notify a third party of the movement, such as by sending an e-mail, automated call, log with the time(s)/place(s) of the detected movement, etc.

In some embodiments, the system may be configured such that the condition is an impermissible location of the laser system. Software in the system may determine the location and the electronic lockout may be executed based on the location. In some embodiments, the sensor may include a GPS receiver. Software in the system may allow any of the following operations: determining the location based on GPS signals received at the GPS receiver and/or executing the electronic lockout when the location of the laser system is outside a permitted area. Examples of a permitted area may include, for example, a treatment room, a treatment facility, or a locality such as a city or country. Other operations may include, in some embodiments, receiving medical record information specifying a desired change in an eye color of a patient extracting, from a database, treatment parameters for changing the eye color with the laser system, where the treatment parameters are based on the medical record information and the location of the laser system. In other implementations, the location may be determined based on triangulation or signal strengths at wireless receivers, such as those utilizing low-energy Bluetooth. In some embodiments, the system may electronically notify a third party of the new location or improper location at an intermediate time. The notification may include, for example, sending an e-mail, automated call, log with the time(s)/place(s) of the determine locations, etc.

FIG. 7 shows an illustrative system for performing an eye color changing procedure in accordance with one or more embodiments. For example, system 700 may represent the components used for performing an eye color changing procedure. For example, system 700 may power a local device to perform an eye color changing procedure where the required determination (e.g., iris mapping, pattern to follow, laser power to deliver, identification of patient, alignment of patient, etc.) are determined remotely and/or in the cloud. As shown in FIG. 7, system 700 may include user terminal 722 and user terminal 724. While shown as personal computers, in FIG. 7, it should be noted that user terminal 722 and user terminal 724 may be any computing device, including, but not limited to, a laptop computer, a tablet computer, a hand-held computer, other computer equipment (e.g., a server), including "smart," wireless, wearable, and/or mobile devices. FIG. 7 also includes cloud components 710. Cloud components 710 may alternatively be any computing device as described above and may include any type of mobile terminal, fixed terminal, or other device. For example, cloud components 710 may be implemented as a cloud computing system and may feature one or more component devices. It should also be noted that system 700 is not limited to three devices. Users may, for instance, utilize one or more other devices to interact with one another, one or more servers, or other components of system 700. It should be noted that, while one or more operations are described herein as being performed by particular components of system 700, those operations may, in some embodiments, be performed by other components of system 700. As an example, while one or more operations are described herein as being performed by components of user terminal 722, those operations may, in some embodiments, be performed by components of cloud components 710. In some embodiments, the various computers and systems described herein may include one or more computing devices that are programmed to perform the described functions. Additionally, or alternatively, multiple users may interact with system 700 and/or one or more components of system 700. For example, in one embodiment, a first user and a second user (e.g., a technician and a physician) may interact with system 700 using two different components.

With respect to the components of user terminal 722, user terminal 724, and cloud components 710, each of these devices may receive content and data via input/output (hereinafter "I/O") paths. Each of these devices may also include processors and/or control circuitry to send and receive commands, requests, and other suitable data using the I/O paths. The control circuitry may comprise any suitable processing circuitry. Each of these devices may also include a user input interface and/or user output interface (e.g., a display) for use in receiving and displaying data. For example, as shown in FIG. 7, both user terminal 722 and user terminal 724 include a display upon which to display data (e.g., information related to an eye color changing procedure).

Additionally, as user terminal 722 and user terminal 724 are shown as touchscreen smartphones, these displays also act as user input interfaces. It should be noted that in some embodiments, the devices may have neither user input interface nor displays and may instead receive and display content using another device (e.g., a dedicated display device such as a computer screen and/or a dedicated input device such as a remote control, mouse, voice input, etc.). Additionally, the devices in system 700 may run an application (or another suitable program). The application may cause the processors and/or control circuitry to perform operations related to an eye color changing procedure.

Each of these devices may also include electronic storages. The electronic storages may include non-transitory storage media that electronically stores information. The electronic storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information obtained from servers, information obtained from client devices, or other information that enables the functionality as described herein.

FIG. 7 also includes communication paths 728, 730, and 732. Communication paths 728, 730, and 732 may include the Internet, a mobile phone network, a mobile voice or data network (e.g., a 7G or LTE network), a cable network, a public switched telephone network, or other types of communications network or combinations of communications networks. Communication paths 728, 730, and 732 may separately or together include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

Cloud components 710 may be a database configured to store user data for a user. For example, the database may include user data that the system has collected about the user through prior operations and/or procedures. Alternatively, or additionally, the system may act as a clearing house for multiple sources of information about the user. Cloud components 710 may also include control circuitry configured to perform the various operations needed to perform an eye color changing procedure.

Cloud components 710 include machine learning model 702. Machine learning model 702 may take inputs 704 and provide outputs 706. The inputs may include multiple data sets such as a training data set and a test data set. Each of the plurality of data sets (e.g., inputs 704) may include data subsets related to user data, an eye color changing procedure, patient progress, and/or results. In some embodiments, outputs 706 may be fed back to machine learning model 702 as input to train machine learning model 702 (e.g., alone or in conjunction with user indications of the accuracy of outputs 706, labels associated with the inputs, or with other reference feedback information). In another embodiment, machine learning model 702 may update its configurations (e.g., weights, biases, or other parameters) based on the assessment of its prediction (e.g., outputs 706) and reference feedback information (e.g., indication of accuracy, results of procedure, reference labels, and/or other information). In another embodiment, where machine learning model 702 is a neural network, connection weights may be adjusted to reconcile differences between the neural network's prediction and the reference feedback. In a further use case, one or more neurons (or nodes) of the neural network may require that their respective errors are sent backward through the neural network to facilitate the update process (e.g., backpropagation of error). Updates to the connection weights may, for example, be reflective of the magnitude of error propagated backward after a forward pass has been completed. In this way, for example, the machine learning model 702 may be trained to generate better predictions (e.g., predictions related to an appropriate iris mapping to use, pattern to follow, laser power, level of eye color change, number of procedures, length of procedures, etc.

In some embodiments, machine learning model 702 may include an artificial neural network. In such embodiments, machine learning model 702 may include an input layer and one or more hidden layers. Each neural unit of machine learning model 702 may be connected with many other neural units of machine learning model 702. Such connections may be enforcing or inhibitory in their effect on the activation state of connected neural units. In some embodiments, each individual neural unit may have a summation function which combines the values of all of its inputs together. In some embodiments, each connection (or the neural unit itself) may have a threshold function such that the signal must surpass before it propagates to other neural units. Machine learning model 702 may be self-learning and trained, rather than explicitly programmed, and may perform significantly better in certain areas of problem solving, as compared to traditional computer programs. During training, an output layer of machine learning model 702 may correspond to a classification of machine learning model 702 and an input known to correspond to that classification may be input into an input layer of machine learning model 702 during training. During testing, an input without a known classification may be input into the input layer, and a determined classification may be output.

In some embodiments, machine learning model 702 may include multiple layers (e.g., where a signal path traverses from front layers to back layers). In some embodiments, back propagation techniques may be utilized by machine learning model 702 where forward stimulation is used to reset weights on the "front" neural units. In some embodiments, stimulation and inhibition for machine learning model 702 may be more free flowing, with connections interacting in a more chaotic and complex fashion. During testing, an output layer of machine learning model 702 may indicate whether or not a given input corresponds to a classification of machine learning model 702 (e.g., an eye color change requested, a pattern to follow, a laser power to deliver, alignment of patient, etc.).

Figure 8:
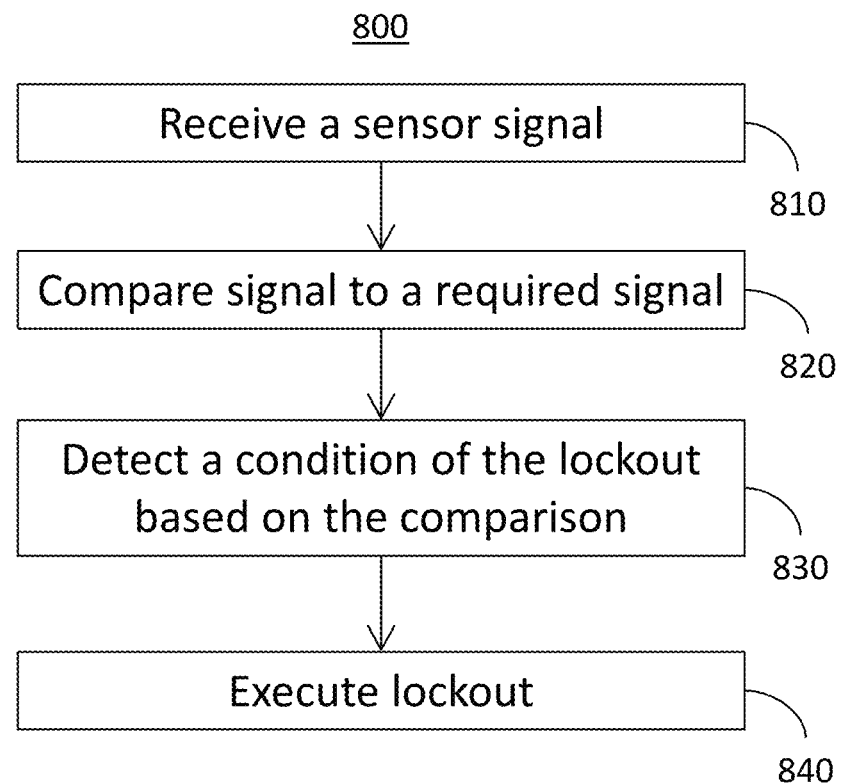
FIG. 8 shows a process for use of a sensor in executing electronic lockouts in accordance with one or more embodiments.

FIG. 8 shows a process 800 for use of a sensor in executing electronic lockouts in accordance with one or more embodiments. As described with reference to FIG. 6, in some embodiments the system (which may include the disclosed laser system) may include a housing around some component(s). The system may also include a perimeter circuit configured to detect a breach of the housing based on the perimeter circuit being broken. In some embodiments, the break may result in an electrical current flowing through the perimeter circuit ceasing (e.g., in energized embodiments as disclosed here). In other embodiments, the break may result in a change in resistance in the perimeter circuit (e.g., in un-energized embodiments disclosed herein). In yet other embodiments, the system may include a sensor configured to detect movement or determine a location of the laser system. In this way, the term "sensor" encompasses embodiments of a perimeter circuit (which in various ways may 'sense' a breach by virtue of being broken) and also includes other types of sensors as described herein (e.g., motion sensors or location sensors). Thus, process 800 (e.g., via one or more components of FIGS. 5-7) may represent the steps taken by one or more devices and/or sensors as shown in FIGS. 5-7 when determining whether to lock out the system so as to not allow an eye color changing procedure.

At step 810, process 800 may (e.g., via one or more components of FIGS. 5-7) receive a sensor signal. For example, in some embodiments, this may include signals reflective of the breaking of a perimeter circuit (e.g., a voltage, current, or resistance change). In other embodiments, the signals may also include electronic signals such as location or movement data.

At step 820, process 800 may (e.g., via one or more components of FIGS. 5-7) compare the sensor signal to a required signal. For example, with a perimeter circuit, the required signal may be a specific characteristic (e.g., voltage, current, or resistance) of the circuit that indicates a breach (or non-breach). These characteristics may be stored at a database that may be accessed via the system (e.g., as presented in FIG. 7). Similarly, the required signal for use with a motion sensor may be data entries indicating permissible motion (e.g., limits to vibrations or machine velocities or accelerations). In some embodiments, the data entries for use of a location sensor may be of permissible locations (e.g., permitted rooms in a building, city, region, etc.) as may be defined electronically in the database to create a virtual geofence such that outside such locations a lockout may be initiated by the system.

While the above steps are described to provide a more fulsome description of some embodiments of the disclosed systems, it is not essential that any particular software embodiment need have those steps. For example, one embodiment of software may include only the following steps, with the preceding steps implemented in other software modules that may or may not be included in any of the claimed embodiments.

At step 830, process 800 may (e.g., via one or more components of FIGS. 5-7) detect a condition of the lockout based on the comparison. For example, the perimeter circuit or other sensor may detect the breach based on the perimeter circuit being broken, an unacceptable location or movement of the laser system as detected by the sensor, etc. The detection of the condition may be based on the comparison by virtue of the comparison providing information needed for the detection. For example, the comparison may indicate that the resistance of the perimeter circuit has increased 1000% (as may be possible if the circuit was heavily damaged, but not completely broken). The detection may then include the system determining that the increase in resistance is above a permissible increase (e.g., 10%, which may be enough to allow for reasonable measurement variations). In other embodiments, where the condition is a location of the laser system, the detection may be based on comparing the instant location to an intended location or area (as accessed via a database). The detection may then include the system calculating that the system location is outside the specified boundary.

At step 840, process 800 may (e.g., via one or more components of FIGS. 5-7) execute a lockout of one or more components of the system. For example, the system may execute a lockout of the laser system based on the breach, or other condition as described herein, such that the laser system cannot be operated without receipt of a command lifting the electronic lockout. As described in more detail with reference to FIG. 5, the lockout may occur in any number of ways. For example, the system may become password locked, a key component (e.g., a Pockels cell of the laser system) may be disabled or rendered essentially inoperable for use in the procedure, user commands (e.g., to start the procedure) may be ignored, configuration or other critical data files may be deleted, pre-existing interrupts in the laser system or power supplies may be triggered, etc.

In various embodiments, other security measures such as multi-factor authentication, authentication based on close proximity wireless communication (e.g., line-of-sight RF transmission or low-energy Bluetooth communications) between a personal computing device (e.g., a dongle or smartphone) and the laser system. Such authentications may be in embodiments where there is a limited temporal window to use authentication keys or passcodes (e.g., 20 minutes).

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

Embodiment 1: A method for altering an eye color of a patient with a color alteration procedure, the method comprising: capturing a first scan with an image sensor and at a first time prior to the altering of the eye color, the first scan being of at least one of an iris or retina of the patient; capturing a second scan with the image sensor and at a second time later than the first time and prior to the altering of the eye color, the second scan being at least one of the iris or the retina of the patient; comparing the first scan captured at the first time with the second scan captured at the second time; determining an identity of the patient based on matching the first scan captured at the first time with the second scan captured at the second time; generating for display, on a user interface, a confirmation of the identity of the patient; and enabling, at a laser system, delivery of laser light by the laser system to the iris or retina of the patient upon confirmation of the identity.

Embodiment 2: The method of any of the preceding embodiments, further comprising: retrieving, from a database and based on the second scan, patient medical record data associated with the color alteration procedure; and displaying the patient medical record data at a console in communication with the laser system.

Embodiment 3: The method of any of the preceding embodiments, further comprising automatically setting a laser power of the laser system based on the patient medical record data and a patient treatment plan.

Embodiment 4: The method of any of the preceding embodiments, wherein the matching is based on comparing a first pattern in the first scan to a second pattern in the second scan, wherein for the second scan being of the iris, the second pattern is based at least partially on stromal pigment fibers in the iris.

Embodiment 5: The method of any of the preceding embodiments, wherein the matching is based on comparing a first pattern in the first scan to a second pattern in the second scan, wherein for the second scan being of the retina, the second pattern is based at least partially on the reflectivity of retinal tissue and blood vessels in the retina.

Embodiment 6: The method of any of the preceding embodiments, further comprising receiving a user input in response to the confirmation to enable the delivery of the laser light.

Embodiment 7: The method of any of the preceding embodiments, further comprising delivering the laser light.

Embodiment 8: A system comprising a laser system for altering the eye color of a patient with a color alteration procedure, the system comprising: a housing around at least one component of the laser system; a perimeter circuit configured to detect a breach of the housing based on the perimeter circuit being broken resulting in an electrical current flowing through the perimeter circuit being ceased or a change in resistance in the perimeter circuit; and at least one programmable processor; and a non-transitory machine-readable medium storing instructions which, when executed by the at least one programmable processor, cause the at least one programmable processor to perform operations comprising: detecting, by the perimeter circuit, the breach based on the perimeter circuit being broken; and executing, based on the breach, an electronic lockout of the laser system such that the laser system cannot be operated without receipt of a command lifting the electronic lockout.

Embodiment 9: The system of any of the preceding embodiments, wherein the perimeter circuit is completed by one or more of a metallic screw, electrical contacts, a breakable conductive wire.

Embodiment 10: The system of any of the preceding embodiments, further comprising a battery operatively connected to the perimeter circuit to energize the perimeter circuit, the operations further comprising executing the electronic lockout when the energy remaining in the battery is below a battery lockout threshold.

Embodiment 11: The system of any of the preceding embodiments, wherein the perimeter circuit is configured to be energized by main power to the laser system and the battery is operatively connected to the perimeter circuit such that when main power is interrupted the battery energizes the perimeter circuit.

Embodiment 12: The system of any of the preceding embodiments, wherein executing the electronic lockout comprises disabling the laser system by controlling a Pockels cell of the laser system to stop or reduce laser power output by the laser system.

Embodiment 13: The system of any of the preceding embodiments, wherein executing the electronic lockout comprises locking out a control system of the laser system to prevent at least one command being accepted that is required for operation of the laser system.

Embodiment 14: The system of any of the preceding embodiments, wherein executing the electronic lockout comprises deletion of a configuration file necessary for operation of the laser system.

Embodiment 15: A system comprising a laser system for altering the eye color of a patient with a color alteration procedure, the laser system comprising: a sensor configured to detect movement or determine a location of the laser system; at least one programmable processor; and a non-transitory machine-readable medium storing instructions which, when executed by the at least one programmable processor, cause the at least one programmable processor to perform operations comprising: detecting, utilizing the sensor, a condition that causes the laser system to initiate an electronic lockout; and executing, based on the condition, the electronic lockout of the laser system such that the laser system cannot be operated without receipt of a command lifting the electronic lockout.

Embodiment 16: The system of any of the preceding embodiments, the operations further comprising electronically notifying a third party of the detection.

Embodiment 17: The system of any of the preceding embodiments, wherein the condition is movement of the laser system, the operations further comprising determining the movement, and the electronic lockout is executed based on the movement.

Embodiment 18: The system of any of the preceding embodiments, wherein the sensor is configured to detect movement comprising lateral movement, vertical movement, or tilting.

Embodiment 19: The system of any of the preceding embodiments, wherein the sensor is configured to detect movement comprising vibrations.

Embodiment 20: The system of any of the preceding embodiments, wherein the sensor comprises a gyroscope or mercury switch.

Embodiment 21: The system of any of the preceding embodiments, wherein the condition is a location of the laser system, the operations further comprising determining the location, and the electronic lockout is executed based on the location.

Embodiment 22: The system of any of the preceding embodiments, wherein the sensor comprises a GPS receiver, the operations further comprising: determining the location based on GPS signals received at the GPS receiver; and executing the electronic lockout when the location of the laser system is outside a permitted area.

Embodiment 23: The system of any of the preceding embodiments, the operations further comprising: receiving medical record information specifying a desired change in an eye color of a patient; and extracting, from a database, treatment parameters for changing the eye color with the laser system, wherein the treatment parameters are based on the medical record information and the location of the laser system.

Embodiment 24: A tangible, non-transitory, machine-readable medium storing instructions that, when executed by a data processing apparatus, cause the data processing apparatus to perform operations described in any of the above system or method embodiments 1-23.

Embodiment 25: A system comprising: one or more processors; and memory storing instructions that, when executed by the processors, cause the processors to effectuate operations described in any of the above system or method embodiments 1-23.

What is claimed is:

1. A method for altering an eye color of a patient with a color alteration procedure that comprises multiple treatments, the method comprising:
    performing, using a laser system, a first treatment of the color alteration procedure on an eye of the patient, wherein the first treatment causes a macrophagic removal of stromal pigment from the eye of the patient;
    after the first treatment and following the macrophagic removal of stromal pigment from the eye of the patient, capturing a first scan with an image sensor, wherein the first scan is of stromal pigment fibers in an iris of the patient;
    storing, in a database, the first scan;
    after storing the first scan and prior to a second treatment of the color alteration procedure, capturing a second scan with the image sensor, wherein the second scan is of the stromal pigment fibers in the iris of the patient;
    comparing the first scan with the second scan;
    determining an identity of the patient based on matching the stromal pigment fibers in the iris of the patient in the first scan with the stromal pigment fibers in the iris of the patient in the second scan;
    generating for display, on a user interface, a confirmation of the identity of the patient; and
    enabling, at the laser system, delivery of laser light by the laser system to the iris the patient to perform the second treatment of the color alteration procedure upon confirmation of the identity.

2. The method of claim 1, further comprising:
    retrieving, from the database and based on the second scan, patient medical record data associated with the color alteration procedure; and
    displaying the patient medical record data at a console in communication with the laser system.

3. The method of claim 2, further comprising automatically setting a laser power of the laser system based on the patient medical record data and a patient treatment plan.

4. The method of claim 1, wherein the matching is based on comparing a first pattern of the stromal pigment fibers in the iris of the patient in the first scan to a second pattern of the stromal pigment fibers in the iris of the patient in the second scan.

5. The method of claim 1, wherein the matching is based on comparing a first pattern of the stromal pigment fibers in the iris of the patient in the first scan to a second pattern of the stromal pigment fibers in the iris of the patient in the second scan using a machine learning model.

6. The method of claim 1, further comprising receiving a user input in response to the confirmation to enable the delivery of the laser light.

7. The method of claim 1, further comprising delivering the laser light.

8. The method of claim 1, further comprising:
    detecting, by a perimeter circuit, a breach based on the perimeter circuit being broken; and
    executing, based on the breach, an electronic lockout of the laser system such that the laser system cannot be operated without receipt of a command lifting the electronic lockout.

9. The method of claim 8, wherein the perimeter circuit is configured to be energized by main power to the laser system and a battery is operatively connected to the perimeter circuit such that when main power is interrupted the battery energizes the perimeter circuit.

10. The method of claim 1, further comprising delivering the laser light, wherein the delivery is of an exposure less than a maximum permissible exposure and causes elimination of at least a portion of stromal pigment.

11. A system for altering an eye color of a patient with a color alteration procedure that comprises multiple treatments, the system comprising:
    a laser system configured to deliver laser light to an iris the patient to perform the color alteration procedure; and
    non-transitory, machine-readable medium storing instructions, which, when executed by at least one programmable processor, cause the at least one programmable processor to perform operation comprising:
        performing, using the laser system, a first treatment of the color alteration procedure on an eye of the patient, wherein the first treatment causes a macrophagic removal of stromal pigment from the eye of the patient;
        after the first treatment and following the macrophagic removal of stromal pigment from the eye of the patient capturing a first scan with an image sensor, wherein the first scan is of stromal pigment fibers in an iris of the patient;
        storing, in a database, the first scan;
        after storing the first scan and prior to a second treatment of the color alteration procedure, capturing a second scan with the image sensor, wherein the second scan is of the stromal pigment fibers in the iris of the patient;
    comparing the first scan with the second scan;
    determining an identity of the patient based on matching the stromal pigment fibers in the iris of the patient in the first scan with the stromal pigment fibers in the iris of the patient in the second scan;
    generating for display, on a user interface, a confirmation of the identity of the patient; and
    enabling, at the laser system, delivery of the laser light by the laser system to the iris the patient to perform the color alteration procedure upon confirmation of the identity.

12. The system of claim 11, further comprising:
    retrieving, from the database and based on the second scan, patient medical record data associated with the color alteration procedure; and
    displaying the patient medical record data at a console in communication with the laser system.

13. The system of claim 12, wherein the instructions further cause operations comprising automatically setting a laser power of the laser system based on the patient medical record data and a patient treatment plan.

14. The system of claim 11, wherein the matching is based on comparing a first pattern of the stromal pigment fibers in the iris of the patient in the first scan to a second pattern of the stromal pigment fibers in the iris of the patient in the second scan.

15. The system of claim 11, wherein the matching is based on comparing a first pattern of the stromal pigment fibers in the iris of the patient in the first scan to a second pattern of the stromal pigment fibers in the iris of the patient in the second scan using a machine learning model.

16. The system of claim 11, wherein the instructions further cause operations comprising receiving a user input in response to the confirmation to enable the delivery of the laser light.

17. The system of claim 11, wherein the instructions further cause operations comprising delivering the laser light.

18. The system of claim 11, wherein the instructions further cause operations comprising:
   detecting, by a perimeter circuit, a breach based on the perimeter circuit being broken; and
   executing, based on the breach, an electronic lockout of the laser system such that the laser system cannot be operated without receipt of a command lifting the electronic lockout.

19. The system of claim 18, wherein the perimeter circuit is configured to be energized by main power to the laser system and a battery is operatively connected to the perimeter circuit such that when main power is interrupted the battery energizes the perimeter circuit.

20. The system of claim 11, wherein the instructions further cause operations comprising delivering the laser light to the patient, wherein the delivery is of an exposure less than a maximum permissible exposure and causes elimination of at least a portion of stromal pigment.

\* \* \* \* \*